(12) United States Patent
Morgan

(10) Patent No.: US 9,421,031 B2
(45) Date of Patent: Aug. 23, 2016

(54) SCALPEL BLADE HOLDER

(76) Inventor: Lee Morgan, Gaithersburg, MD (US)

( * ) Notice: Subject to any disclaimer, the term of this patent is extended or adjusted under 35 U.S.C. 154(b) by 1369 days.

(21) Appl. No.: 11/694,040

(22) Filed: Mar. 30, 2007

(65) Prior Publication Data

US 2008/0243158 A1 Oct. 2, 2008

(51) Int. Cl.
*A61B 17/3213* (2006.01)
(52) U.S. Cl.
CPC ................. *A61B 17/3213* (2013.01)
(58) Field of Classification Search
CPC .................................... A61B 17/3213
USPC ............ 606/167, 170, 172, 190, 138; 30/294; 128/898
See application file for complete search history.

(56) References Cited

U.S. PATENT DOCUMENTS

| 3,054,182 | A | * | 9/1962 | Whitton, Jr. ............... 606/138 |
| 3,287,751 | A | | 11/1966 | Hoffman |
| 3,672,054 | A | | 6/1972 | Kaufman |
| 4,026,295 | A | * | 5/1977 | Lieberman .................. 606/167 |
| 4,034,473 | A | * | 7/1977 | May .............................. 606/138 |
| 4,053,979 | A | * | 10/1977 | Tuthill et al. ............... 606/138 |
| 4,432,138 | A | * | 2/1984 | Piccolo, Jr. ................. 30/294 |
| 4,473,076 | A | * | 9/1984 | Williams et al. ............ 606/172 |
| 5,085,663 | A | * | 2/1992 | Tarr ............................. 606/172 |
| 5,122,152 | A | * | 6/1992 | Mull ............................ 606/170 |
| 5,253,659 | A | * | 10/1993 | McNamara et al. .......... 128/898 |
| 5,341,822 | A | * | 8/1994 | Farr et al. ................... 128/898 |
| 5,356,419 | A | * | 10/1994 | Chow .......................... 606/170 |
| 5,507,800 | A | * | 4/1996 | Strickland ................... 606/167 |
| 5,737,842 | A | | 4/1998 | Freedman |
| 5,769,866 | A | * | 6/1998 | Frantzen ..................... 606/167 |
| 5,827,311 | A | * | 10/1998 | Berelsman et al. .......... 606/167 |
| 6,019,774 | A | * | 2/2000 | Weiss et al. ................. 606/167 |

* cited by examiner

*Primary Examiner* — Thomas McEvoy
(74) *Attorney, Agent, or Firm* — Paul Hastings, LLP

(57) ABSTRACT

A scalpel blade holder including a handle, a blunt probe, and a blade. A method of using the scalpel blade holder including inserting the blunt probe into a small incision, and advancing the scalpel blade holder to create the incision.

18 Claims, 2 Drawing Sheets

SCALPEL BLADE HOLDER

BACKGROUND OF THE INVENTION

1. Field of the Invention

Devices, systems, and methods consistent with the invention relate to a scalpel blade handle.

2. Description of the Related Art

A wide variety of scalpel blade handles have been developed for surgical applications (e.g., veterinary and human surgery). One example is the Parker-Kerr scalpel blade handle, which has a simple handle with a clip at one end that holds a replaceable scalpel blade.

However, these tools are deficient in some respects. For example, in small animal medicine, surgery often involves operation on patients less that 10 kg that lack substantial intra-abdominal fat. When performing procedures such as laparotomies (or other abdominal surgeries where the abdomen must be entered through a ventral midline incision) on these patients, there is potential for injury to the patient unless the scalpel user is very careful.

More specifically, a traditional technique for these procedures is to tent (i.e., pinch) the area of the desired incision using forceps (or the surgeon's thumb and forefinger), and to then apply pressure using a standard scalpel blade handle to make an incision through the linea alba. Unfortunately, in small animals where the intra-abdominal fat pad is not well developed, excessive downward pressure may result in inadvertent trauma to vital abdominal organs (e.g., the jejunum, which lies very close to the linea alba in small animals). Such trauma to internal organs during the entry procedure raises morbidity and mortality risks.

In addition, this traditional technique is inefficient because it requires the use of two different instruments to make the initial intra-abdominal incision—the scalpel blade and forceps (or the surgeon's thumb and forefinger). This is both inefficient and awkward for the surgeon.

Similar problems are also found in human surgeries, where the same risk factors apply. These risks are especially pronounced in emaciated, geriatric, or neonatal humans which, like small animals, have very little intra-abdominal fat to protect internal organs and internal organs.

Thus, injury to vital internal structures is a serious concern to the operating surgeon using a traditional scalpel blade handle. This demands an improvement in the related art system.

BRIEF SUMMARY OF THE INVENTION

According to an aspect of the invention, there is provided a scalpel blade holder, including: a handle; a blunt probe; and a blade.

According to another aspect of the invention, there is provided a method of using a scalpel blade holder including: a handle; a blunt probe; and a blade to make an incision, the method including inserting the blunt probe into a small incision, and advancing the scalpel blade holder to create the incision.

The above stated aspect, as well as other aspects, features and advantages of the invention will become clear to those skilled in the art upon review of the following description.

BRIEF DESCRIPTION OF THE DRAWINGS

The above and/or other aspects of the invention will be more apparent by describing in detail exemplary embodiments of the invention with reference to the accompanying drawings, in which.

DETAILED DESCRIPTION OF EXEMPLARY EMBODIMENTS

Figure 1:
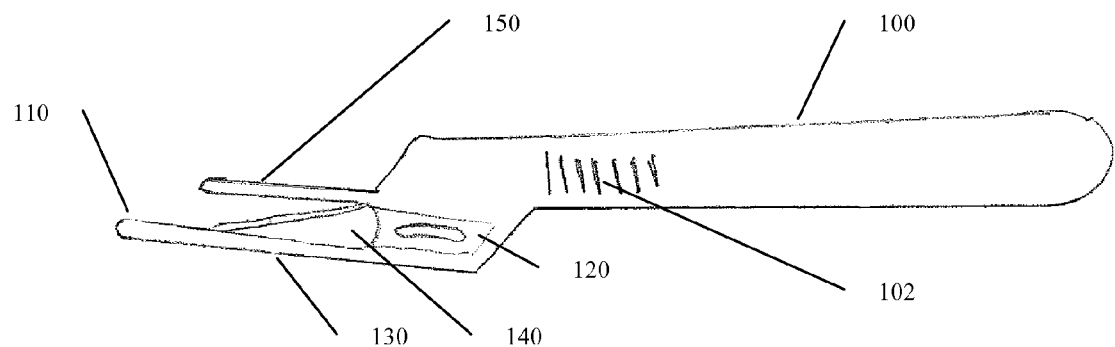
FIG. 1 illustrates a scalpel blade holder according to an exemplary embodiment of the invention.

Exemplary embodiments of the invention will now be described below by reference to the attached Figures. The described exemplary embodiments are intended to assist the understanding of the invention, and are not intended to limit the scope of the invention in any way. Like reference numerals refer to like elements throughout.

As described above, the use of a traditional scalpel blade holder when performing surgery in some contexts is dangerous and inefficient. The inventive scalpel blade holder eliminates these deficiencies by incorporating a design that allows the surgeon to cut away from vital internal organs. This makes inadvertent laceration or blunt trauma to abdominal organs unlikely, and also increases the efficiency of the surgical cut, because a secondary instrument, such as forceps or the surgeon's forefingers, are no longer required.

An exemplary embodiment of the inventive scalpel blade holder is shown in FIG. 1. In this embodiment, a handle 100 includes, at one end, blunt probe 110, upper prong 150, and lower prong 130. A clip 120 in situated on a lower prong 130, and provides for removable attachment of a scalpel blade 140 (e.g., a #11 scalpel blade). The handle 100 extends from the terminus of the bifurcation of the upper and lower prongs 150, 130. The scalpel blade handle 100 may be angled slightly upward to facilitate an upward directed cutting vector at the scalpel blade/tissue interface. Handle 100 may include raised finger grips 102.

In operation, the surgeon may grasp the handle 100 with his thumb on the dorsal aspect of the instrument and extended toward to front of the instrument, although other methods of grasping consistent with the use of the invention are acceptable. The blunt probe 110 of the device is then inserted into a cavity (e.g., a small keyhole incision) where an incision axis has been determined. The surgeon then can advance the device forward along the incision axis, while possibly exerting some upward pressure (depending upon the particular application). The blunt probe 110 tents the intended cutting structure, freeing it from underlying or surrounding soft tissue and/or vascular supply, and directing it toward the cutting edge of scalpel blade 140. The blunt probe 110 also gently moves vital organs and such away from the cutting edge of scalpel blade 140. The upper prong 150 also guides and compresses tissues to the scalpel blade 140, providing some measure of hemostasis as well. After the cut is completed, the device may be withdrawn in a typical fashion. The scalpel blade may then be removed and the instrument may be cleaned and sterilized as other typical surgical instruments.

This design produces a very clean, surgical grade incision, and does not require the use of a separate surgical instrument (such as tissue or thumb forceps) to make the initial intra abdominal incision or to extend such incision. This is advantageous because it allows the surgeon greater control. Cleaner cuts reduce wound healing time.

Various embodiments of this device may be of different sizes, optimized for use with different sized patients.

In another exemplary embodiment, probe 110 and/or lower prong 130 may have a triangular cross section to facilitate soft tissue dissection, while maintaining the probe 110's primary function of pushing away vital tissue.

Figure 2:
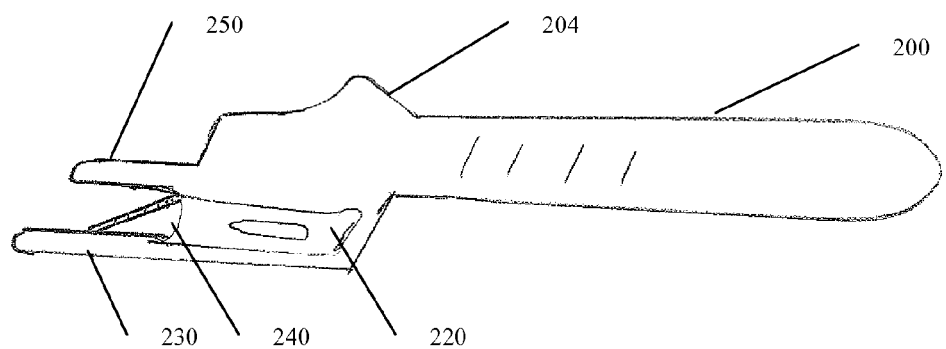
FIG. 2 illustrates a scalpel blade holder according to another exemplary embodiment of the invention.

In another exemplary embodiment, as shown in FIG. 2, handle 200 may include thumb rest 204, arranged to allow greater dexterity with the instrument. Clip 220, upper prong 250, scalpel blade 240, and lower prong 230 are similar to the embodiments shown above.

Figure 3:
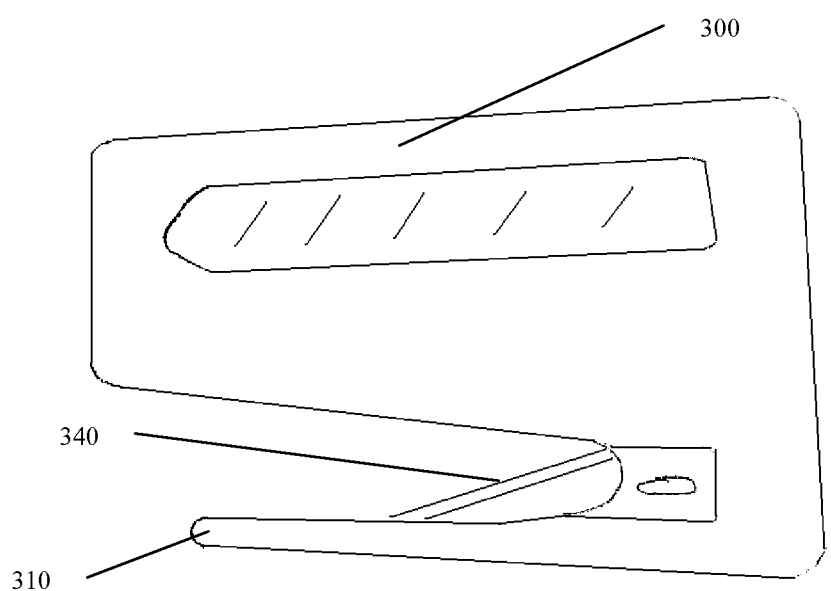
FIG. 3 illustrates a scalpel blade holder according to another exemplary embodiment of the invention.

In another exemplary embodiment, as shown in FIG. 3, handle 300 may be situated over probe 310 and blade 340. This arrangement allows the deletion of the upper prong (e.g., 150 in FIG. 1) in the previously described embodiments, since the handle assumes the function of directing and compressing tissue to the cutting surface of the scalpel blade. This arrangement may also be more comfortable for some surgeons.

The entire inventive scalpel holder may be fabricated from surgical stainless steel to allow ease of cleaning and sterilization of the instrument. Surgical stainless steel is also highly durable, which allows extended use of the device through many procedures.

As described above, the inventive design is safer and allows for more precise, cleaner surgical cuts. Because the instrument requires only one hand to operate, the surgery is inherently more efficient.

In addition to the advantages discussed above, this new design is advantageous in intricate intra abdominal surgeries such as splenectomies or appendectomies where the organ is highly vascular and delicate. The vessels leading to and from the organ lie in close proximity to one another. If a vessel is inadvertently lacerated prior to being ligated, the patient may lose a rapid amount of blood in a short period of time. The improved design presented here lessens the chance of inadvertent laceration of vital vessels, allows the surgeon to bluntly dissect fibrous and connective tissue surrounding vital vessels and allows the surgeon greater visibility prior to making decisive incisions.

This new design is also well adapted for hollow organ surgery such as gastratomies or bladder surgeries. In these procedures, the traditional approach is to blindly stab into the lumen of the organ, tent the incision line with a pair of forceps, and make an entry incision. This traditional procedure is flawed because it takes two hands to make one incision, and the initial incision in done blindly, without the surgeon knowing what lies below the entry incision. Thus, it is possible that the hollow organ contents may spill into the abdominal cavity, even if the organ is properly packed off. Use of the improved scalpel design makes hollow organ surgery more efficient and safer, because, after a small pinhole entry hole is made into the organ, the surgeon merely needs to insert the blunt end of the instrument into the lumen of the hollow organ, and advance the instrument forward. This makes a more precise entry incision and allows the tent of the intended tissue to be cut without the use of a secondary surgical instrument, such as thumb forceps. This frees the surgeons other hand for other procedures, perhaps to prevent accidental leakage of hollow organ contents into the peritoneal cavity.

Still further, in intestinal surgical procedures such as jejunotomies or jejunectomies, the traditional procedure demands the surgeon first clamp off the area where the surgery is to take place. Since a jejunotomy, such as required when performing a foreign body, is similar in procedure to that of a typical hollow organ surgery, the advantages of the improved scalpel blade handle will not be repeated here, except to point out that a longitudinal incision can be made with greater control and ease. In the case of a jejunotomy with an anastomosis, the traditional technique demands that a surgeon make saw-like motions through the entire structure with the same hazards described above. Often the resultant surgical margins are ragged because of this technique. In addition, the jejunotomy is a blind procedure in that the surgeon cannot visually inspect the contents of the organ prior to making and/or extending a surgical incision. This complication is avoided by using the advanced design presented here, because the surgeon merely lifts the length of bowel to be transected, and advances the instrument forward to complete a clean edge incision. This technique allows unseen foreign objects or unidentified areas of tissue to be safely moved aside, rather than being accidentally incised. The surgical procedure using the new scalpel blade provides a cleaner cut edge, unlike the ragged edge to the tissue that occurs when tissue is sawed through. Anastomosis surgeries are generally more successful when the opposing edges are clean, rather than ragged. This is because a tighter junction may be achieved when there are no gaps between the opposing ends.

While the invention has been particularly shown and described with reference to exemplary embodiments thereof, the invention is not limited to these embodiments. It will be understood by those of ordinary skill in the art that various changes in form and details may be made therein without departing from the spirit and scope of the invention as defined by the following claims.

The invention claimed is:

1. A scalpel blade holder, comprising: a handle; a blunt probe extending straightly in a first direction; and a blade having a cutting edge extending straightly in a second direction facing away from the blunt probe, wherein the blunt probe has a triangular cross section.

2. The scalpel blade holder described in claim 1, wherein the handle further comprises raised finger grips.

3. The scalpel blade holder described in claim 1, wherein the handle further comprises a thumb rest.

4. The scalpel blade holder described in claim 1, wherein the handle extends in a direction opposite the blunt probe.

5. The scalpel blade holder described in claim 1, wherein the handle extends in the same direction as the blunt probe.

6. The scalpel blade holder described in claim 5, further comprising a lower prong, wherein: the lower prong forms the blunt probe; and the blade is arranged between the lower prong and the handle.

7. The scalpel blade holder described in claim 6, wherein the cutting edge of the blade faces away from the lower prong, and faces towards the handle.

8. The scalpel blade holder described in claim 1, further comprising a clip, wherein the blade is removably provided in the clip.

9. The scalpel blade holder described in claim 1, further comprising a lower prong, wherein: the lower prong extends in a first direction and forms the blunt probe; and the blade is arranged on the lower prong.

10. The scalpel blade holder described in claim 9, wherein the cutting edge of the blade faces away from the lower prong.

11. The scalpel blade holder described in claim 8, wherein the distal end of the blunt probe is rounded and extends beyond a distal end of the blade.

12. The scalpel blade holder described in claim 1, further comprising an upper prong and a lower prong; wherein: the lower prong extends in a first direction and forms the blunt probe; the upper prong extends in the first direction; and the blade is arranged between the upper and lower prongs.

13. The scalpel blade holder described in claim 12, wherein the cutting edge of the blade faces away from the lower prong, and faces towards the upper prong.

14. The scalpel blade holder described in claim 1, wherein the distal end of the blunt probe is rounded and extends beyond a distal end of the blade.

15. A method of using a scalpel blade holder comprising a handle; a blunt probe extending straightly in a first direction; and a blade having a cutting edge extending straightly in a second direction facing away from the blunt probe to make an incision, the method comprising inserting the blunt probe into a small incision, and advancing the scalpel blade holder in an advancing direction parallel to the first direction to create the incision, wherein, when the scalpel blade holder is advanced to create the incision, the blunt probe lifts at least a skin layer and guides the skin layer to the blade.

16. The method described in claim 15, further comprising exerting upward pressure.

17. The method described in claim 15, wherein the blunt probe separates at least an organ from the skin layer.

18. The scalpel blade holder described in claim 15, wherein the incision is a keyhole incision through an outer skin or organ layer.

\* \* \* \* \*